United States Patent [19]

Nappholz et al.

[11] 4,378,020
[45] Mar. 29, 1983

[54] DUAL CHAMBER PACER

[75] Inventors: Tibor A. Nappholz, Drummoyne; Bruce R. Satchwell, Pymble; David K. Money, Pennant Hills, all of Australia

[73] Assignee: Telectronics Pty. Ltd., Lane Cove, Australia

[21] Appl. No.: 294,751

[22] Filed: Aug. 20, 1981

[51] Int. Cl.³ .............................................. A61N 1/36
[52] U.S. Cl. ............................................. 128/419 PG
[58] Field of Search .................. 128/419 PG, 419 PT

[56] References Cited

U.S. PATENT DOCUMENTS

| | | | |
|---|---|---|---|
| 3,747,604 | 7/1973 | Berkovits | 128/419 PG |
| 3,783,878 | 1/1974 | Thaler et al. | 128/419 PG. |
| 4,114,627 | 9/1978 | Lewyn et al. | 128/419 PT |
| 4,166,470 | 9/1979 | Neumann | 128/419 PG |
| 4,248,238 | 2/1981 | Joseph | 128/419 PG |
| 4,328,807 | 5/1982 | Jirak et al. | 128/419 PG |

*Primary Examiner*—William E. Kamm
*Attorney, Agent, or Firm*—Gottlieb, Rackman & Reisman

[57] ABSTRACT

There is disclosed a dual chamber pacer which offers several advantages over prior art devices. Although the pacer requires for its operation AV delay and VA delay parameter values, most physicians characterize dual chamber pacers in terms of AV delay and ventricular pacing rate. The pacer of the invention can be programmed under external control by the physician setting values for the parameters with which he is most familiar. A subtractor in the pacer forms the difference between the reciprocal of the ventricular pacing rate and the AV delay to derive the value of the VA delay. The pacer is also characterized by active recharge of the atrial output capacitor so that a very short ventricular refractory period following atrial pacing may be provided. A single maximum rate timer prevents the generation of excessively fast ventricular stimuli, whether due to the ventricular or atrial sub-systems, or even if atrial contractions are being sensed at too rapid a rate.

10 Claims, 1 Drawing Figure

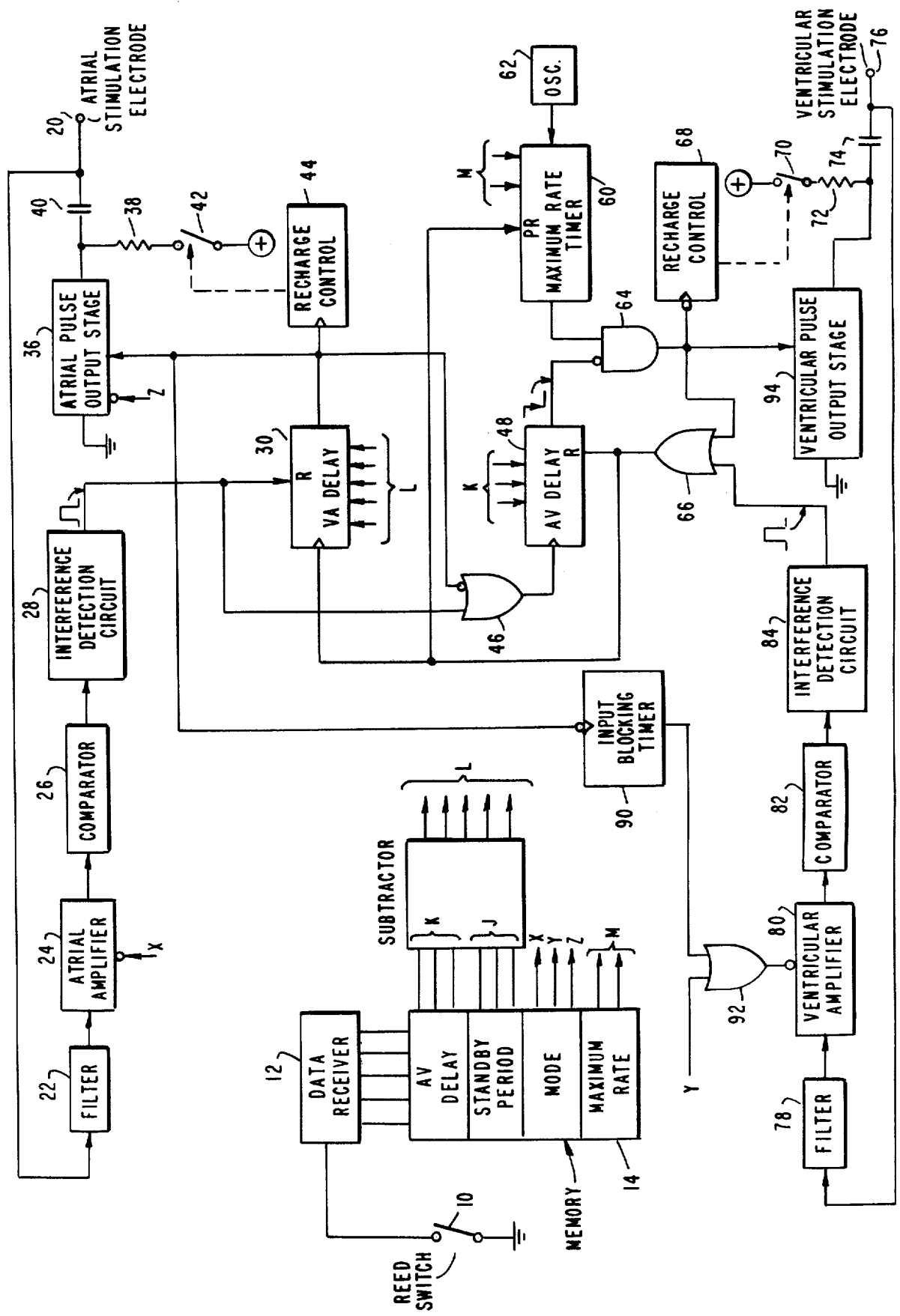

DUAL CHAMBER PACER

DESCRIPTION

This invention relates to dual chamber heart pacers, and more particularly to such pacers which are externally programmable.

Single chamber heart pacers, especially those which provide for ventricular stimulation, have enjoyed widespread use for many years. More recently, considerable attention is being paid to dual chamber pacers. Such a pacer is provided with atrial as well as ventricular electrodes. (Unipolar or bipolar leads may be used for each chamber, as desired). Each electrode serves not only to provide a stimulus to a respective chamber, but also to sense spontaneous heart activity.

Typically, two delay circuits are provided. The VA (ventricular-atrial) delay circuit, or timer, is triggered by either a spontaneous ventricular beat or a ventricular stimulus, the latter being generated in the event the heart ventricles did not contract spontaneously. Following the VA delay, an atrial stimulating pulse is generated. However, if a spontaneous atrial contraction occurs prior to the expiration of the VA delay, then an atrial stimulus is not generated. The AV (atrial-ventricular) delay circuit is triggered by either a spontaneous atrial contraction or the generation of an atrial stimulus, the latter taking place in the event the atria did not contract spontaneously. Following expiration of the AV delay, a ventricular stimulus is generated; if during the AV delay a spontaneous ventricular contraction occurred, then a stimulus is not generated. A typical dual chamber heart pacer can be operated in several different modes, as will be described below, under external program control. The different modes are achieved by selectively disabling atrial chamber sensing, ventricular chamber sensing, and atrial stimulus generation.

Not only can the mode of operation of a typical dual chamber pacer be programmed, but so can several other parameters. Just as in the case of a single chamber pacer, an external programmer may be used by a physician to control such things as the pacer rate, sensitivity, etc. Two of the most important parameter values in the case of a dual chamber pacer are the VA delay and the AV delay. Once these values are set under external control, they are used by the pacer until another programming sequence takes place. There is a simple relationship between the VA and AV delays, and the overall pacing rate. The latter is simply the rate of ventricular stimuli, the reciprocal of which is known as the "R-R" interval. The sum of the VA and AV delays equals the R-R interval.

The actual parameter values which directly control the pacer operation are the VA and AV delays. Most physicians, however, do not think of heart pacing in these terms. They tend to characterize pacing in terms of the AV delay and the pacing rate. While the arithmetic involved in determining the VA delay from the other two parameter values is not that complicated, it would be advantageous to allow a physician to program a pacer with the actual parameters which he uses to characterize its operation. In the prior art, however, dual chamber pacers have not been programmable in terms of AV delay and pacer rate parameters. (The R-R interval, also known as the "standby period", is simply the reciprocal of the pacer rate. It makes no difference whether a rate or an interval value is programmed, since the conversion from one to the other simply involves forming a reciprocal—either in the programmer or the pacer. The problem is that the pacer requires a VA value, and physicians don't usually think in such terms.)

It is a general object of our invention to provide an externally programmable, implantable dual chamber pacer whose AV and VA delays are controlled by programmed parameter values for AV delay and pacer rate. (A further advantage of the scheme used to accomplish this object is that less memory is required in the pacer to store the programmed information, as will be described below.)

In accordance with the principles of our invention, this first object is accomplished by providing a subtractor circuit in the pacer. The programmed parameter values are the AV delay and the standby period. The subtractor forms the difference between the standby period and the AV delay, the difference being the VA delay which is used to control the time period between a ventricular beat (spontaneous or stimulated) and the generation of an atrial stimulus. It is by providing an on-board subtractor that the physician can program the pacer in the terms with which he is familiar, yet the pacer can be controlled to operate directly from the parameter values which it requires.

Another problem with prior art dual chamber pacers relates to their excessively long ventricular amplifier blanking following an atrial pacing pulse. In order to prevent a large-magnitude atrial stimulating pulse which is applied to the patient's heart from being interpreted by the ventricular sensing circuit as a ventricular contraction, the sensing circuit is usually disabled for a refractory period which begins immediately before the atrial stimulus. A typical atrial stimulus may generate a disturbance in the ventricular sensing circuit for 100 milliseconds due to the nature of the electrode recovery waveform. To inhibit the ventricular sensing circuit for 100 milliseconds following each atrial stimulus, so that the atrial stimulus will itself not be sensed as a ventricular contraction, may actually result in a failure to detect a ventricular beat should it occur during the long refractory period.

It is another object of our invention to provide a dual chamber pacer in which the need to prevent an atrial stimulus from being interpreted as a ventricular beat does not give rise to a significant number of spontaneous ventricular beats not being sensed.

This is accomplished in accordance with the principles of our invention by controlling each atrial stimulus recovery waveform to be much shorter than those found in the prior art. In the illustrative embodiment of our invention the atrial stimulating pulse recovery waveform has a duration of only 10–15 milliseconds, and the refractory period which starts with the leading edge of the pulse, during which period the ventricular sensing circuit is disabled, has a duration of only 25 milliseconds. The extra 10–15 milliseconds is provided as a margin of safety. In general, we contemplate the generation of an atrial stimulus and an associated refractory period, both of which are no longer than 40 milliseconds.

In a typical prior art pacer, there is an output capacitor in series with each electrode lead. Following the generation of a pulse, the capacitor is charged to the battery potential. When a stimulating pulse is to be generated, the capacitor is allowed to discharge through the electrode lead and the heart tissue. The capacitor is usually returned through a resistor of about 15 kilohms to the battery supply. The leading edge of the stimulating pulse is usually quite sharp, and it is the recovery waveform on the trailing edge whose slope gives rise to the excessively long disturbance in the ventricular sensing circuit. In accordance with the principles of our invention, the capacitor is returned to the battery supply through a much lower impedance, typically 400 ohms, so that the recovery waveform on the trailing edge of the pulse is shortened. It is in this way that an atrial stimulating pulse may be generated with a recovery waveform whose overall duration is only in the order of 10–15 milliseconds, and consequently the ventricular sensing circuit only needs to be disabled for this time.

It is to be noted that a similar technique has been used in the prior art in connection with ventricular pulse generation. In some cases, the output capacitor connected in series with the ventricular electrode lead has been returned to the battery supply through a low impedance. The reason for this has been to allow the input impedance of the ventricular sensing circuit to be high for as much of the time as is possible; the input impedance is usually lower while the output capacitor is charging, and by increasing the charging rate the input impedance is at a relatively low value for much less time. This technique is known as "active" recharge of the output capacitor, "active" because the output capacitor is returned through a low impedance to the battery supply as opposed to the conventional higher impedance. We utilize a similar technique in connection with the atrial pulsing circuit, although for a totally different reason, as described above.

It is relevant to note that the addition of pull-up in the ventricular output stage ensures that various artifacts from the supply, the most predominant being the recharging of the decoupling capacitor, are prevented from being sensed by the ventricular channel after atrial pacing. This modification allows higher ventricular sensitivities for the same ventricular blanking time.

Still another problem with dual chamber pacers pertains to the prevention of excessively fast ventricular stimuli. Even in the case of a single chamber pacer, there is the possibility that the oscillator which controls the rate at which ventricular pulses are generated may develop a fault, in which case ventricular stimuli may be generated at a dangerously fast rate. For this reason, a separate runaway-protection mechanism is usually provided to ensure that ventricular pulses are not generated at a rate faster than a maximum safe value. It is apparent that in a dual chamber pacer there is yet another possible source which might cause a ventricular pulse runaway condition; excessively fast spontaneous atrial contractions or an electronic fault which shortens the VA delay can both give rise to excessively fast triggerings of the AV delay, which in turn can cause successive ventricular stimuli to be generated at too fast a rate.

It is another object of our invention to provide a dual chamber pacer in which a single, simple fail-safe mechanism functions to limit the rate of the ventricular stimuli under all of the fault conditions described above.

Further objects, features and advantages of our invention will become apparent upon consideration of the following detailed description in conjunction with the drawing which depicts, in symbolic form only, the illustrative embodiment of our invention.

Atrial stimulation electrode 20 is connected in the patient's heart to stimulate an atrial contraction. When switch 42 is closed, current flows from the pacer battery through resistor 38, capacitor 40 and the atrial electrode lead to charge the capacitor. (Switch 42 is shown only symbolically, it being understood that in a practical pacer an electronic switch would be provided.) The switch is held closed by recharge control element 44 in order to recharge the capacitor following an atrial stimulating pulse. When an atrial stimulus is to be generated, as determined by the output of VA delay circuit 30 going low, atrial pulse output stage 36 connects capacitor 40 to a negative potential equal to the battery voltage in magnitude; the capacitor discharges through the patient's heart to stimulate an atrial beat. The atrial pulse output stage operates, however, only if its Z control input is low in potential. If the Z input is high, no atrial stimuli are generated.

The output of VA delay unit 30 is normally high. When the output of OR gate 66 first goes high and triggers the VA delay timing, the output of delay unit 30 remains high. But after a time interval determined by the five bits at input L of the delay unit, the output is pulsed low. The leading edge of the negative pulse triggers atrial pulse output stage 36 to connect capacitor 40 to a negative potential for about 0.5 milliseconds, provided that the Z input is low in potential. The trailing edge causes recharge control element 44 to close switch 42 for 10–15 milliseconds. After 10–15 milliseconds, the recharge control element opens switch 42 so that the input impedance of the atrial stimulating electrode 20 is returned to greater than 100 kilohms.

Atrial electrical activity at electrode 20 appears at the input of RF filter 22, and after filtering the signal is amplified by atrial amplifier 24. The amplifier functions, however, only if the X control input is low in potential. The output of the amplifier is compared by comparator 26 to a threshold value, and a standard interference detection circuit 28 operates to reject high-frequency noise; pulses at the output of comparator 26 which arrive with 200 milliseconds of each other are ignored by circuit 28. The net result, as is standard in the art, is that a spontaneous atrial beat results in a short positive pulse at the output of interference detection circuit 28. This pulse is used to reset VA delay circuit 30. Even if the delay circuit was timing a VA interval, following the last ventricular beat and leading up to an atrial stimulus which is to be generated, the timing mechanism is reset so that an atrial stimulating pulse is not generated. There is no need for such a pulse inasmuch as a spontaneous atrial beat has been detected.

A comparable sub-system is provided for generating ventricular stimuli and for detecting spontaneous ventricular contractions. The details of the operation of AV delay unit 48 will be described below, but for present purposes it is sufficient to understand that whenever a ventricular stimulus is to be generated, the output of gate 64 is pulsed high to turn on ventricular pulse output stage 94. The charge on capacitor 74 now causes current to flow through the ventricular stimulation electrode 76. After the pulse is generated, element 68 causes switch 70 to close so that capacitor 74 can recharge through resistor 72. The switch is opened again after 10–15 milliseconds to return the input impedance of the ventricular stimulating electrode 16 to greater than 100 kilohms. Filter 78, ventricular amplifier 80, comparator 82 and interference detection circuit 84 correspond to elements 22, 24, 26 and 28 in the atrial stimulation sub-system. The ventricular amplifier operates to detect ventricular beats only if the Y input to gate 92 is low in potential; if it is high, amplifier 80 is inhibited from operating.

Before proceeding to a description of the remainder of the circuit, it will be helpful to understand the six modes in which the system can be operated, depending upon the levels of the control signals at the X, Y and Z inputs discussed above.

When the X and Z inputs are high, and the Y input is low, ventricular sensing is enabled, but atrial sensing and atrial stimulation are both inhibited. This is known as the VVI mode, the overall unit functioning as a standard ventricular demand pacer. With respect to the three letters which characterize each mode, the first refers to the chamber which is paced (with the symbol "D" representing both), the second refers to the chamber whose activity is sensed (with the letter "D" once again representing both), and the third represents what functions result from the sensing. In the VVI mode, there is ventricular pacing, ventricular sensing, and "inhibited" operation; following the detection of a spontaneous ventricular beat, the ventricular timing circuit (AV delay unit 48) is prevented from triggering a ventricular stimulus since a spontaneous beat has already occurred.

In the DVI mode, the X input is high, and the Y and Z inputs are both low; atrial sensing is still prevented, but now atrial stimuli are generated as well as ventricular stimuli. Following the detection of a ventricular stimulus, the VA delay timer 30 is triggered. At the end of the VA delay, an atrial stimulus is generated; it is always generated after the time-out, because the atrial sensing is inhibited so that interference detection circuit 28 cannot reset VA delay unit 30. After the atrial stimulus is generated, the AV delay timing begins, and at the end of the AV delay a ventricular stimulus is generated. Because ventricular sensing takes place, however, the ventricular stimulus is generated only if a spontaneous ventricular beat is not detected before the AV delay time-out. This mode is also popularly known as the "bifocal" mode.

When the X and Y control bits are both low and the Z control bit is high, there is no atrial pulsing but there is atrial as well as ventricular sensing—the VDI mode. The V represents ventricular pacing, the D represents atrial and ventricular sensing, and the I represents inhibition of ventricular pacing should a spontaneous ventricular beat be detected. This mode is also known as the "AV sync" mode because ventricular pacing is synchronized to atrial activity. Following the detection of spontaneous atrial contraction, the AV delay timing begins. If the AV delay period times out before a spontaneous ventricular beat is detected, a ventricular stimulus is generated. If a ventricular beat is detected first, a ventricular stimulus is not generated. In either case, the VA delay timer 30 is triggered, but it has no effect because no atrial stimuli are generated. The system simply waits until it detects a spontaneous atrial beat, following which the AV delay timing begins once again.

When each of the control bits is a 0, the system operates in the DDD mode. There are both atrial and ventricular sensing, and atrial and ventricular pacing. Both pulse sequences are on demand, in that the detection of spontaneous atrial or ventricular activity results in the resetting of the respective timer so that the next stimulus which would otherwise have been generated is inhibited.

When all three control bits are high, the system operates in the V00 mode. Each ventricular pulse triggers the VA delay, after the VA time-out the AV delay is triggered, and after the AV time-out a ventricular stimulus is generated and the cycle repeats itself. This is nothng more than continuous ventricular pacing.

The last mode in which the system can be operated is that in which the X and Y control bits are high, and the Z control bit is low. In this D00 mode, there is continuous atrial pacing as well as continuous ventricular pacing. There is no sensing of heart activity; at the end of the VA delay, an atrial stimulus is generated and the AV delay timing begins, and at the end of the AV delay, a ventricular stimulus is generated and the VA delay timing begins.

At the left of the drawing there is shown a reed switch 10. This reed switch is pulsed by an external programmer as is known in the art. Data receiver 12 interprets the pulse closures and applies address and data signals to memory 14. The memory stores four types of information. Three "mode" bits are stored, and these are the bits which determine the levels of the X, Y and Z control lines discussed above. The physician can thus determine the mode in which the pacer operates, and he can change the mode even after implantation.

Another three bits are stored in the memory to represent the AV delay. These three bits are represented by the letter K, and they are shown as inputs to AV delay unit 48. Eight possible AV delay values can be programmed by the physician.

The physician also programs one of eight allowable basic pacer rates. Although the programmer unit itself typically has numerical indicia which represent rate, what is really programmed when the physician selects a rate value is the R-R interval. This is the reciprocal of the rate, and it is also known as the "standby period". Data receiver 12 stores three bits in memory 14 which represent the R-R interval, and these three bits are represented by the letter J.

The last two bits which are stored in the memory are depicted by the letter M, and they represent the maximum pacing rate. There are three maximum ventricular rates which the physician can select, and two bits are required to represent them. (Other programmable parameters, such as atrial sensitivity, are not depicted inasmuch as they are not pertinent to the subject invention. It is to be understood, however, that in actual practice a full range of programming capability may be provided.)

The physician can select from among eight different standby periods, and eight different AV delays. Subtractor 16 forms the difference between the standby period and the AV delay, and thus it really forms a value which represents the VA delay necessary to have the programmed values of AV delay and standby period. Since there are eight possible AV delay values and eight possible standby period values, it might be thought that there could be 64 different differences; however, with conventional AV delay and standby period values, it turns out that many of the differences are the same. For example, an R-R interval of 800 milliseconds and an AV delay of 200 milliseconds provide the same VA delay of 600 milliseconds that results when the R-R interval is 700 milliseconds and the AV delay is 100 milliseconds. Only five bits are required to specify all of the possible VA delay values, and thus there are only five bits at the output of the subtractor, designated by the letter L. These five bits are applied to VA delay timer 30 to control the VA delay interval.

It should be noted that the three bits for the AV delay timer are actually programmed by the physician, since he selects the AV delay directly. The pacer requires five bits to represent the VA delay value. The physician does not usually think in terms of VA delay, and instead characterizes a pacer with respect to its AV delay and R-R interval (or pacing rate). The use of the subtractor allows the physician to program parameters with which he is most familiar. It is the subtractor which derives the VA delay value. Another advantage of programming the AV delay and R-R interval values, rather than the AV delay and VA delay values, is that only six memory bits (K plus J) are required instead of eight (K plus L).

It will be recalled that when the output of VA delay unit 30 is first pulsed low, output stage 36 is turned on for about 0.5 milliseconds and control element 44 closes switch 42 when the output stage turns off. The control element returns to its normal state after about 10-15 milliseconds. The negative pulse at the output of delay unit 30 also triggers input blocking timer 90. This timer, after being triggered, causes its output to go high for 25 milliseconds. The high potential extended through OR gate 92 disables ventricular amplifier 80. Thus the ventricular refractory period, during which ventricular sensing is disabled so that the atrial stimulus will not be erroneously interpreted as representing a ventricular beat, is much shorter than the refractory periods used in the prior art. The reason that a shorter period is possible is that resistor 38 has a value of only about 400 ohms. The atrial output pulse recovery waveform is very short in duration because the active pull-up of capacitor 40 allows it to recharge very rapidly. Once the capacitor has recharged, there is no need for further ventricular sensing inhibition.

The output of VA delay unit 30 is connected to the inverting input of OR gate 46. Consequently, at the end of the VA delay the output of gate 46 goes high to trigger the AV delay timer 48. In the event atrial sensing is not inhibited, each spontaneous atrial contraction results in a pulse at the output of interference detection circuit 28. This pulse serves two functions. First, it resets VA delay unit 30 so that its output does not go low as it otherwise would at the end of the VA interval; since a spontaneous atrial contraction has been detected, there is no need for an atrial stimulus, even if the Z control bit is low to otherwise allow one. The second function of the pulse at the output of interference detection circuit 28 is to trigger the AV delay unit 48 through OR gate 46. Whenever an atrial connection takes place, whether it be caused by the generation of an atrial stimulus or having been spontaneous, the AV delay timing begins.

The AV delay timer is different from the VA delay timer. The output of the latter is normally high, and it is pulsed low only momentarily following a time-out. The AV delay unit, on the other hand, has its output latched low at the end of its time-out. Assuming that the output of maximum rate timer 60 is high so that one input of gate 64 is enabled, when the output of the AV delay timer goes low, the inverting input of gate 64 is enabled and its output goes high. As described above, this results in a ventricular stimulus being generated. The same pulse is extended through OR gate 66 to reset the AV delay timer whose output goes high once again. Similarly, if a spontaneous ventricular beat is detected, the short pulse at the output of interference detection circuit 84 is extended through OR gate 66 to reset the AV delay timer, whose output goes high once again. In this way, a spontaneous ventricular beat prevents the generation of a ventricular stimulus.

Whether a spontaneous ventricular beat occurs or a ventricular stimulus is generated, the pulse at the output of OR gate 66 is extended to the trigger input of VA delay unit 30. Consequently, the ventricular-atrial timing sequence begins so that another atrial stimulus can be generated (assuming that the Z control bit is low) if a spontaneous atrial contraction is not detected (assuming that the X control bit is low) prior to the VA delay time-out.

The same pulse at the output of OR gate 66 which triggers the VA delay timing is applied to the preset input of maximum rate timer 60. This device is simply a down counter whose count is decremented by output pulses from oscillator 62. The initial count loaded in the timer when the preset input is pulsed is determined by the two M bits. The physician can select from one of three maximum rates, ventricular pacing not being allowed to exceed this rate even should something go wrong with data receiver 12 or AV delay unit 48. The lower the maximum rate programmed by the physician, the longer it takes for timer 60 to be decremented down to a value of 0, i.e., the higher the count which is preset. The output of timer 60 remains low until the count is decremented all the way down to zero, and it then remains high until the preset input is pulsed once again. Consequently, even if the output of AV delay unit 48 goes low, a ventricular stimulus cannot be generated for as long as the output of timer 60 is low. It is only after timer 60 has been decremented down to a count of zero that a low signal at the inverting input of gate 64 can cause the output of the gate to go high. Since the down counting begins with a ventricular beat, inasmuch as the presetting of timer 60 is controlled by the pulse at the output of OR gate 66, it is apparent that the initial count preset in timer 60 determines the maximum rate at which ventricular pulses can be generated.

This fail-safe mechanism prevents ventricular stimuli from being generated at a dangerously fast rate even if the AV delay somehow fails to a negligible value (due to an electrical short, a faulty data receiver, etc.). But the same mechanism also prevents ventricular run-away which might otherwise be caused by atrial "problems". Suppose, for example, that the VA delay unit does not function properly, and that the VA delay period is much shorter than it is programmed to be. While it is true that an atrial pulse will be generated too soon after ventricular sensing, if the Z control bit is low, that pulse will not necessarily result in excessively fast ventricular beating (the really dangerous condition); the AV delay timer 48 is triggered prematurely, but ventricular pulses cannot be generated at a rate faster than that allowed by the maximum rate timer 60. The timer always begins counting from the last ventricular beat, and it does not allow a ventriclar stimulus to be generated before it has counted down to zero. Similar remarks apply if spontaneous atrial contractions are occurring at too rapid a rate. The AV delay unit 48 will be re-triggered at a similarly rapid rate. Even assuming that the output of delay unit 48 has already gone low when each input trigger arrives so that re-triggering takes place, ventricular stimuli cannot occur at a rate faster than that represented by the maximum rate bits in memory 14.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A dual chamber heart pacer having a ventricular-atrial delay timer and an atrial-ventricular delay timer, means operative following operation of said ventricular-atrial delay timer for selectively generating an atrial stimulus and for triggering operation of said atrial-ventricular delay timer, means operative following operation of said atrial-ventricular delay timer for generating a ventricular stimulus and for triggering operation of said ventricular-atrial delay timer, means responsive to externally transmitted signals for representing an atrial-ventricular delay value to be used by said atrial-ventricular delay timer, means responsive to externally transmitted signals for representing a ventricular-ventricular pacing interval, and subtractor means for forming the difference between said ventricular-ventricular pacing interval and said atrial-ventricular delay value for deriving a ventricular-atrial delay value to be used by said ventricular-atrial delay timer.

2. A dual chamber heart pacer in accordance with claim 1 wherein said atrial-ventricular delay value and said ventricular-ventricular pacing interval are both represented by respective groups of data bits, the difference formed by said subtractor means being similarly represented by a respective group of data bits, and the number of data bits required to represent said difference is greater than the number of data bits required to represent said ventricular-ventricular pacing interval.

3. A dual chamber heart pacer in accordance with claim 2 further including means for sensing ventricular heart activity and in response thereto for preventing the generation of a ventricular stimulus and for triggering operation of said ventricular-atrial delay timer, means for controlling the duration of each atrial stimulus and the attendant recovery waveform to be less than 40 milliseconds, and means for inhibiting operation of said sensing means for no longer than 40 milliseconds following the start of the generation of each atrial stimulus.

4. A dual chamber heart pacer in accordance with claim 3 further including maximum-rate timer means triggerable together with triggering of said ventricular-atrial delay timer, and means for preventing the generation of a ventricular stimulus following operation of said atrial-ventricular delay timer until said maximum-rate timer means has timed out.

5. A dual chamber heart pacer in accordance with claim 1 further including means for sensing ventricular heart activity and in response thereto for preventing the generation of a ventricular stimulus and for triggering operation of said ventricular-atrial delay timer, means for controlling the duration of each atrial stimulus and the attendant recovery waveform to be less than 40 milliseconds, and means for inhibiting operation of said sensing means for no longer than 40 milliseconds following the start of the generation of each atrial stimulus.

6. A dual chamber heart pacer in accordance with claim 5 further including maximum-rate timer means triggerable together with triggering of said ventricular-atrial delay timer, and means for preventing the generation of a ventricular stimulus following operation of said atrial-ventricular delay timer until said maximum-rate timer means has timed out.

7. A dual chamber heart pacer in accordance with claim 1 further including maximum-rate timer means triggerable together with triggering of said ventricular-atrial delay timer, and means for preventing the generation of a ventricular stimulus following operation of said atrial-ventricular delay timer until said maximum-rate timer means has timed out.

8. A dual chamber heart pacer comprising means for selectively generating an atrial stimulating pulse, means for selectively sensing atrial heart activity, means for generating a ventricular stimulating pulse, means for selectively sensing ventricular heart activity, means for controlling the generation of an an atrial stimulating pulse at a first predetermined time following the sensing of ventricular heart activity, means for controlling the generation of a ventricular stimulating pulse at a second predetermined time following the sensing of atrial heart activity, said atrial stimulating pulse generating means including a storage capacitor which discharges to generate an atrial stimulating pulse and allows the attendant waveform recovery in less than 40 milliseconds and means for controlling the recharging of said capacitor without disturbing the sensing of subsequent signals, and means for inhibiting operation of said ventricular heart activity sensing means for no more than 40 milliseconds following the start of the discharge of said storage capacitor.

9. A dual chamber heart pacer in accordance with claim 8 further including timing means triggerable by the sensing of ventricular heart activity or the generation of a ventricular stimulating pulse, and means for preventing the generation of a ventricular stimulating pulse until after said timing means has timed out.

10. A dual chamber heart pacer comprising means for selectively generating an atrial stimulating pulse, means for selectively sensing atrial heart activity, means for generating a ventricular stimulating pulse, means for selectively sensing ventricular heart activity, means for controlling the generation of an atrial stimulating pulse at a first predetermined time following the sensing of ventricular heart activity, means for controlling the generation of a ventricular stimulating pulse at a second predetermined time following the sensing of atrial heart activity, timing means triggerable by the sensing of ventricular heart activity or the generation of a ventricular stimulating pulse, and means for preventing the generation of a ventricular stimulating pulse until after said timing means has timed out.

* * * * *